US009962546B2

(12) United States Patent
Carroll et al.

(10) Patent No.: US 9,962,546 B2
(45) Date of Patent: May 8, 2018

(54) CUTANEOUS FIELD STIMULATION WITH DISPOSABLE AND RECHARGEABLE COMPONENTS

(71) Applicant: Meagan Medical, Inc., Vancouver, WA (US)

(72) Inventors: William J. Carroll, LaCenter, WA (US); Mark Edward Schoening, Portland, OR (US); Patrick Allen Scranton, Vancouver, WA (US); William Richard Huseby, Vancouver, WA (US)

(73) Assignee: Meagan Medical, Inc., Vancouver, WA (US)

( * ) Notice: Subject to any disclaimer, the term of this patent is extended or adjusted under 35 U.S.C. 154(b) by 109 days.

(21) Appl. No.: 14/181,004

(22) Filed: Feb. 14, 2014

(65) Prior Publication Data

US 2014/0236258 A1 Aug. 21, 2014

Related U.S. Application Data

(60) Provisional application No. 61/767,509, filed on Feb. 21, 2013.

(51) Int. Cl.
*A61N 1/00* (2006.01)
*A61N 1/36* (2006.01)
*A61N 1/04* (2006.01)

(52) U.S. Cl.
CPC ....... *A61N 1/36021* (2013.01); *A61N 1/0456* (2013.01); *A61N 1/0476* (2013.01); *A61N 1/0492* (2013.01); *A61N 1/36014* (2013.01)

(58) Field of Classification Search
CPC . A61N 1/36021; A61N 1/0456; A61N 1/0476
USPC ........................................................... 607/46
See application file for complete search history.

(56) References Cited

U.S. PATENT DOCUMENTS

| 4,793,353 A | 12/1988 | Borkan |
| 4,837,049 A | 6/1989 | Byers et al. |
| 4,867,166 A | 9/1989 | Axelgaard et al. |
| 4,920,968 A | 5/1990 | Takase |
| 4,969,468 A | 11/1990 | Byers et al. |
| 5,350,414 A | 9/1994 | Kolen |
| 5,449,378 A | 9/1995 | Schouenborg |

(Continued)

FOREIGN PATENT DOCUMENTS

| CA | 2584722 A1 | 4/2006 |
| CN | 1135722 | 11/1996 |

(Continued)

OTHER PUBLICATIONS

International Search Report and Written Opinion for PCT/US2014/017445 dated Jun. 9, 2014 (14 pages).

*Primary Examiner* — Amanda Patton
*Assistant Examiner* — Philip C Edwards
(74) *Attorney, Agent, or Firm* — McDonnell Boehnen Hulbert & Berghoff LLP

(57) ABSTRACT

A CFS system includes self-adhesive, disposable pads. Each pad is combined with a sealed, cleanable battery/controller pod and then placed on the body where needed. The battery/controller pod preferably has wireless capability, such as Bluetooth® capability. The patient can download an application to a smartphone or similar mobile device to control the pods.

13 Claims, 6 Drawing Sheets

(56) References Cited

U.S. PATENT DOCUMENTS

| | | | |
|---|---|---|---|
| 5,772,688 A | 6/1998 | Muroki | |
| 5,928,144 A | 7/1999 | Real | |
| 6,044,286 A | 3/2000 | Ogama | |
| 6,083,253 A | 7/2000 | Ogama | |
| 6,277,116 B1 | 8/2001 | Utely et al. | |
| 6,445,955 B1 * | 9/2002 | Michelson | A61N 1/36003 607/2 |
| 6,609,018 B2 | 8/2003 | Cory et al. | |
| 6,647,296 B2 | 11/2003 | Fischell et al. | |
| 6,690,959 B2 | 2/2004 | Thompson | |
| 6,785,569 B2 | 8/2004 | Schmidt et al. | |
| 6,821,281 B2 | 11/2004 | Sherman et al. | |
| 6,918,907 B2 | 7/2005 | Kelly et al. | |
| 7,212,865 B2 | 5/2007 | Cory | |
| 7,457,667 B2 | 11/2008 | Skiba | |
| 8,086,322 B2 | 12/2011 | Schouenborg | |
| 8,386,005 B2 | 2/2013 | Schouenborg | |
| 8,417,352 B2 | 4/2013 | Carroll et al. | |
| 2002/0120260 A1 | 2/2002 | Morris | |
| 2002/0028991 A1 | 3/2002 | Thompson | |
| 2002/0077688 A1 * | 6/2002 | Kirkland | A61N 1/0452 607/142 |
| 2002/0120261 A1 | 8/2002 | Morris et al. | |
| 2003/0050548 A1 | 3/2003 | Schmidt et al. | |
| 2004/0164454 A1 | 8/2004 | Gartstein et al. | |
| 2004/0181216 A1 | 9/2004 | Kelly et al. | |
| 2005/0043775 A1 | 2/2005 | John et al. | |
| 2005/0075670 A1 | 4/2005 | Bengtsson | |
| 2005/0203366 A1 | 9/2005 | Donoghue et al. | |
| 2006/0047194 A1 | 3/2006 | Grigorov | |
| 2006/0079946 A1 | 4/2006 | Gavronsky et al. | |
| 2006/0085056 A1 | 4/2006 | Schouenborg | |
| 2006/0111626 A1 | 5/2006 | Rossing et al. | |
| 2006/0149341 A1 | 7/2006 | Palti | |
| 2006/0173261 A1 | 8/2006 | Kall et al. | |
| 2007/0015984 A1 | 1/2007 | Yeo et al. | |
| 2007/0106359 A1 | 5/2007 | Schaer et al. | |
| 2007/0123766 A1 | 5/2007 | Whalen et al. | |
| 2007/0169333 A1 | 7/2007 | Donoghue et al. | |
| 2007/0238944 A1 | 10/2007 | Axelgaard | |
| 2007/0265692 A1 | 11/2007 | Koop et al. | |
| 2007/0270927 A1 | 11/2007 | Fisk | |
| 2007/0276318 A1 | 11/2007 | Henley | |
| 2008/0161874 A1 | 7/2008 | Bennett et al. | |
| 2008/0207985 A1 | 8/2008 | Farone | |
| 2010/0264097 A1 | 10/2010 | Sun et al. | |
| 2010/0274327 A1 * | 10/2010 | Carroll | A61N 1/0456 607/72 |
| 2011/0082413 A1 | 4/2011 | Ready et al. | |
| 2012/0109233 A1 | 5/2012 | Lee et al. | |
| 2013/0096641 A1 * | 4/2013 | Strother | A61N 1/36021 607/46 |
| 2014/0207219 A1 * | 7/2014 | Dunbar | A61F 7/007 607/112 |

FOREIGN PATENT DOCUMENTS

| | | |
|---|---|---|
| CN | 101124010 A | 2/2008 |
| CN | 101939049 A | 1/2011 |
| EP | 0275642 A1 | 7/1988 |
| EP | 1809370 A1 | 7/2007 |
| HK | 1118024 A | 1/2009 |
| JP | 01164373 A | 6/1989 |
| JP | 2004-216031 | 8/2004 |
| JP | 2008516724 T | 5/2008 |
| JP | 2009202020 A | 9/2009 |
| KR | 10-2007-0112760 | 11/2007 |
| WO | WO-9323112 A1 | 11/1993 |
| WO | WO 2001/78834 | 10/2001 |
| WO | WO-02089911 A1 | 11/2002 |
| WO | WO-2004020040 A2 | 3/2004 |
| WO | WO-2006043885 A1 | 4/2006 |
| WO | WO-2007136657 A2 | 11/2007 |
| WO | WO 2010/014259 | 2/2012 |
| WO | WO 2012/052986 | 4/2012 |

\* cited by examiner

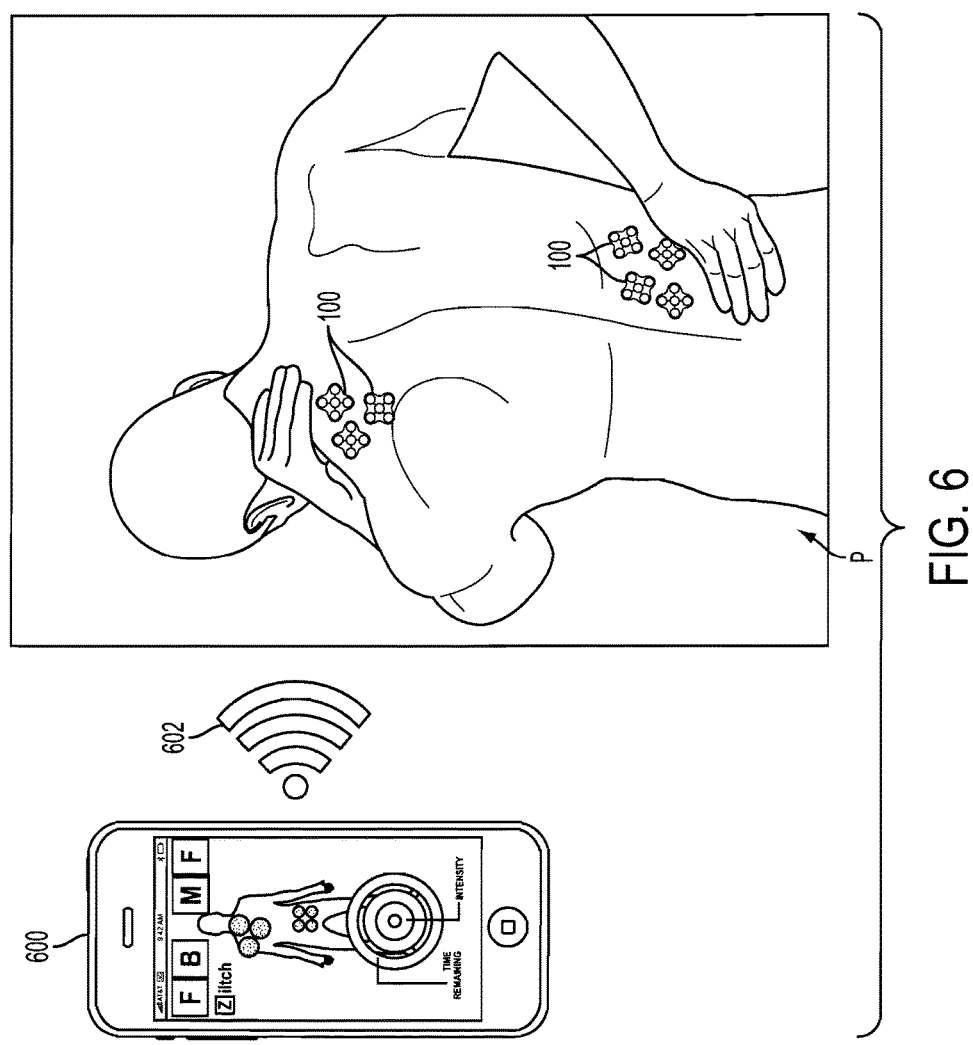

CUTANEOUS FIELD STIMULATION WITH DISPOSABLE AND RECHARGEABLE COMPONENTS

REFERENCE TO RELATED APPLICATIONS

The present application claims the benefit of U.S. Provisional Patent Application No. 61/767,509, filed Feb. 21, 2013. Related subject matter is disclosed in U.S. Patent Application Publication No. 2010/0274327 A1 and in U.S. Pat. Nos. 8,086,322 and 8,386,005. The disclosures of all of the above applications and patents are hereby incorporated by reference in their entireties into the present disclosure.

FIELD OF THE INVENTION

The present invention is directed to cutaneous field stimulation and more particularly to such stimulation with disposable and rechargeable components.

DESCRIPTION OF RELATED ART

Electroanalgesic therapies are known nonpharmacologic alternatives to conventional analgesic drugs for the management of acute and chronic pain. For example, percutaneous electrical nerve stimulation (PENS) is a known form of electroanalgesic therapy typically used for the treatment of intractable pain associated with chronic low back pain syndrome by stimulating the spinal cord (SCS) using electrodes implanted percutaneously into the epidural space as a trial before a more permanent total implantation of an SCS System. The term PENS has also been used to describe a technique for inserting 32-gauge acupuncture needles into soft tissues or muscles to electrically stimulate peripheral nerve fibers in the sclerotomal, myotomal, or dermatomal distribution corresponding to a patient's pain symptoms. Medical devices having arrays of percutaneous electrodes that utilize microstructure needles, which are less invasive than deeper-penetrating acupuncture needles, have also been used for delivering PENS. The microstructure needles provide sufficient penetration to overcome the electrical impedance of the skin tissue for effectively recruiting sensory fibers.

As the understanding of the topographical organization of nociceptive systems becomes more detailed, the target location of the stimulation, the percutaneous electrodes' depth of penetration, and the current amplitude become more exacting. Percutaneous neuromodulation therapy (PNT) and cutaneous field stimulation (CFS) are specific forms of PENS that have been developed using that understanding. PNT is used for the treatment of cervical and lumbar pain and utilizes longer, acupuncture-type needles having a depth of penetration into the skin tissue of up to 3 cm. CFS is used more generally to treat pain and itch and utilizes an array of microstructure needles introduced close to the nerve endings in the skin. Because of the stringent requirements established for needle electrodes by the Food and Drug Administration (FDA) regarding the packaging, sterilization, reuse, and disposal of such electrodes, treatments utilizing such electrodes have generally been administered under the supervision of a physician (e.g., in a doctor's office or a clinic).

CFS is used to assist in the management of chronic nociceptive and neuropathic pain based on the understanding that specific types of sensory nerves that are linked to diminishing the perception of pain can be activated by low amplitude, long duration electrical stimulation if electrodes having sharp tips (i.e., microstructure needles) are introduced close to the nerve endings in the skin. CFS treatment also influences specific active components necessary for perceiving itch by inducing long lasting inhibitory mechanisms in central pathways and by actually normalizing the number of epidermal sensory fibers in itchy skin. Accordingly, CFS also provides an alternative to known treatments for localized itch.

The sensory receptors stimulated by CFS are axons within the skin tissue known as nociceptors, specifically Aδ and C nerve fibers. The stimulation of Aδ and C nerve fibers, although effective in diminishing the perceptions of both pain and itch, can be a relatively uncomfortable treatment because a prickling and/or burning sensation is perceived from the stimulation of the Aδ and C nerve fibers, which can be uncomfortable and painful. Because the aversiveness of Aδ and C nerve fiber stimulation can be masked by Aβ fiber stimulation, it would be a considerable advantage to combine Aδ fiber stimulation (e.g., transcutaneous electrical nerve stimulation (TENS)) and Aδ and C fiber stimulation (e.g., CFS) in the same equipment. Accordingly, there is a need for a method and device that combines Aβ fiber stimulation and Aδ and C fiber stimulation in one treatment. Moreover, there is a need for a method and device that combines TENS and CFS in one treatment.

Cutaneous Field Stimulation (CFS) is a technique for relieving itch and pain that allows topographically restricted and tolerable electrical stimulation of thin (Aδ and C) cutaneous fibers but is not well suited for the stimulation of Aβ fibers. CFS uses a flexible plate with multi-array needle-like electrodes regularly fixed at 2-cm intervals. Each electrode is surrounded by an elevated "stop-device" about 2.0 mm in diameter that protrudes 2.0 mm from the plate. The electrode tip usually protrudes 0.3 mm to 0.4 mm from the stop-device. When gently pressing the electrode plate against the skin, the electrode tips are introduced close to the receptors in the epidermis and the superficial part of dermis. Since the electrodes traverse the electrically isolating horny layer of the epidermis and the current density is high near the sharp electrode tips, the voltage and current required for stimulating cutaneous nerve fibers are small, typically less than 50 V and up to 2 mA, respectively. As the current density decreases rapidly with distance, localized stimulation is achieved. The electrodes are stimulated consecutively with a constant current stimulator, each electrode with a frequency of 1-10 Hz (pulse duration 1.0 ms) and treatment duration of 5-45 min. In its original embodiment, a self-adhesive surface (TENS) electrode served as anode and was usually placed about 5-30 cm away from the needle electrode plate.

Recent improvements in CFS are taught, e.g., in U.S. Pat. No. 8,086,322. However, it would be helpful to provide a CFS system that is less expensive and more easily used than present systems.

CFS works best on pain or itch that is focused in one main area. Therefore, one of the challenges of using CFS for itch or pain that is not focused in one particular area is the distribution of the signal. CFS is most effective when placed directly over the area of pain or itch. Therefore, pain or itch that is distributed over multiple areas requires repeated use of the stimulator serially in each zone of pain or itch. Having a system that would allow simultaneous stimulation of multiple sites with an easy to use interface would be advantageous.

SUMMARY OF THE INVENTION

It is therefore an object of the invention, in at least some embodiments, to provide a system using less expensive pads.

It is another object of the invention, in at least some embodiments, to provide such a system that is easier and more convenient for the patient to use.

It is still another object of the invention, in at least some embodiments, to provide such a system that uses, as its controller, a device that the patient will likely already own, such as a smartphone.

To achieve the above and other objects, the present invention, in at least some embodiments, is directed to a CFS system having self-adhesive, disposable pads. Each pad is combined with a sealed, cleanable battery/controller pod and then placed on the body where needed.

The battery/controller pod preferably has wireless capability, such as Bluetooth® capability. The patient can download an application to a smartphone or similar mobile device (e.g., iPhone, iPad, or Android smartphone). The application guides the patient in the placement of the pads and then controls the smartphone or other mobile device to connect with the battery/controller pods wirelessly and to act as a central controller for the battery/controller pods. The use of that application allows both easy upgradability and a user-friendly graphical user interface and also makes use of a device that the patient likely already has and with which the patient is familiar.

The patient is also provided with an inductive charger for the battery/controller pods. The inductive charger can also have cleaning capability. Once the treatment is over, the patient discards the pads and places the pods into the charger.

A CFS system that has multiple channels with a fewer number of needle like (NL) electrodes per electrode plate (4 to 6 instead of 14 to 16) could be tailored to more effectively treat each zone of pain or itch by titrating the level of stimulation or amplitude for each channel or zone. The size of the treatment zone could also be increased or decreased by adding multiple disposable electrode plates to match the size of the pain or itch zone. The level of stimulation or amplitude of each electrode plate could be individually adjusted and tuned to provide the optimal amount needed at each zone. Using a remote controller (e.g., a smartphone) to adjust the output and parameters of each zone and connecting the controller with each of the electrode plates using Bluetooth or other wireless technology would greatly increase the convenience and ease of use of the CFS system. This type of CFS system would provide a more effective and easier to use treatment of pain and itch due to its scalability, convenience and adjustability.

BRIEF DESCRIPTION OF THE DRAWINGS

A preferred embodiment of the present invention will be set forth in detail with reference to the drawings, in which:

FIG. 6 is a drawing showing the smartphone running the CFS application, the communication between the mobile device and the pads, and the placement of the pads on the patient's body;

DETAILED DESCRIPTION OF THE PREFERRED EMBODIMENT

Figure 1:
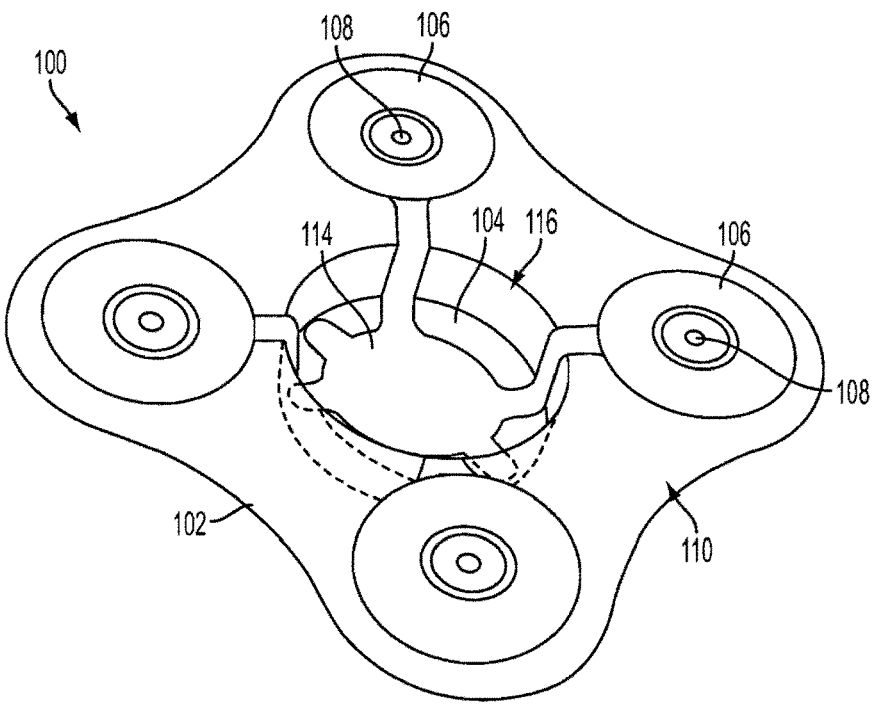
FIG. 1 is a drawing showing the configuration of a pad.

A preferred embodiment of the present invention and variations thereof will be set forth in detail with reference to the drawings, in which like reference numerals refer to like elements or steps throughout.

FIG. 1 shows a pad 100 according to the preferred embodiment. The pad 100 includes a substrate 102 carrying a flexible circuit 104, TENS pads 106, and CFS needle electrodes 108. An adhesive 110 is applied to allow adhesion to the patient's skin, and a cover 112 (not shown in FIG. 1, but shown in FIG. 7B) is disposed on the pad 100. The flexible circuit 104 has a portion 114 formed in a pocket 116 in the substrate 102 to receive power from a pod (to be described below).

The pad 100 is consumable, disposable, and self-adhesive. It has a flexible circuit, one-use gel pads, and one-use CFS needle electrodes.

Figure 2:
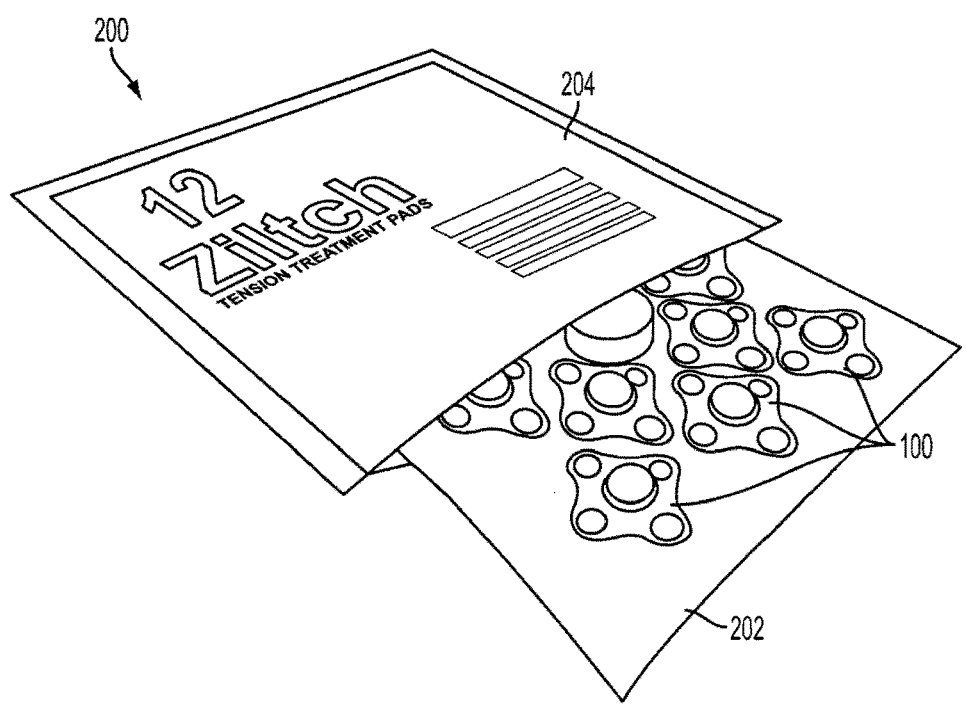
FIG. 2 is a drawing showing a retail package in which the pads are sold to the patient.

FIG. 2 shows multiple pads 100 in an over-the-counter consumer 12-pack 200 having a sheet 202 and an envelope 204. Of course, the pads 100 could be packaged singly or in any number, and the configuration of the packaging can be changed as desired as long as the pads 100 are adequately protected.

Figure 3:
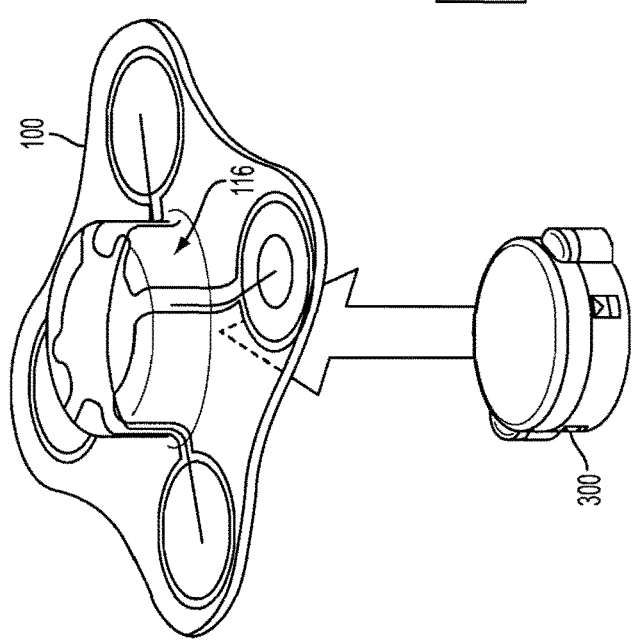
FIG. 3 is a drawing showing the way in which the pad and the pod are combined for use.

FIG. 3 shows a pod 300 for use with the pad 100. The pod 300 is reusable and rechargeable and is inserted into the pocket 116 of the pad 100. The pod 300 can have a surface antimicrobial treatment to assure cleanliness and decrease any possibility of contamination. In addition, or instead, a disinfecting device, to be described below, can be used, or the pods can be wiped with disinfecting cloths between uses.

Figure 4:
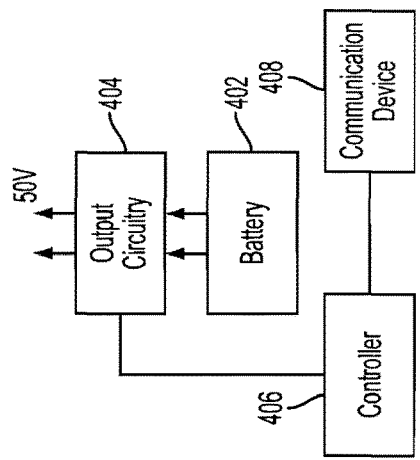
FIG. 4 is a schematic diagram showing the circuitry in the pod of FIG. 3.

FIG. 4 is a circuit diagram showing the circuitry contained in the pod 300. The pod 300 contains a 3V battery 402 and output circuitry 404 for providing a 50V output. The battery 402 has a life of 20 minutes and operates under control of a microelectronic controller 406 and a Bluetooth communication device 408. Of course, any suitable values and any suitable communication protocol could be used instead.

Figure 5:
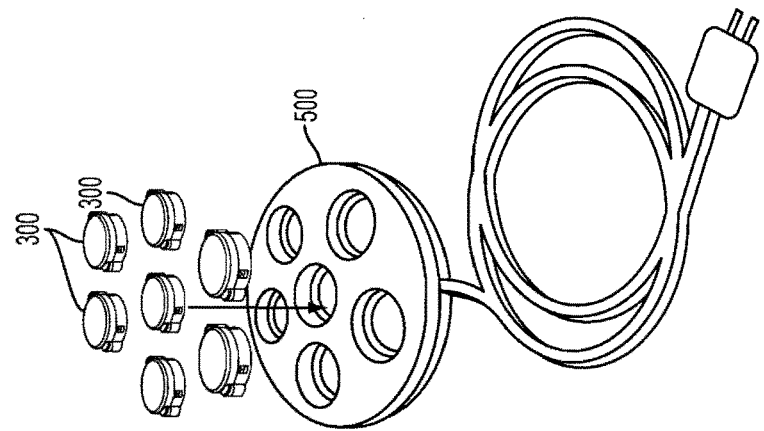
FIG. 5 is a drawing showing the way in which the pods are placed into the charger after use.

FIG. 5 shows an inductive pod charger 500 into which multiple pods 300 are inserted for inductive charging.

FIG. 6 shows multiple pads 100 placed on the back of a patient P. A suitably programmed smartphone or other wireless device 600 communicates with the pods (not shown in FIG. 6) using a Bluetooth connection 602.

Figure 7A:
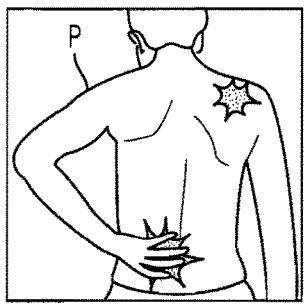
FIGS. 7A through 7L are diagrams showing steps in the use of the CFS system.
Figure 7B:
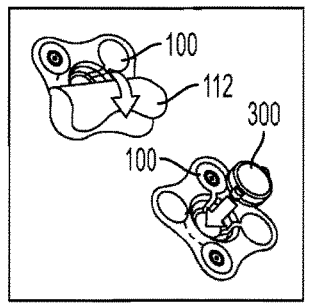
Figure 7C:
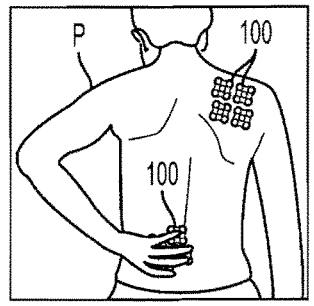
Figure 7D:
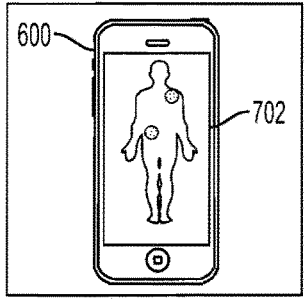
Figure 7E:
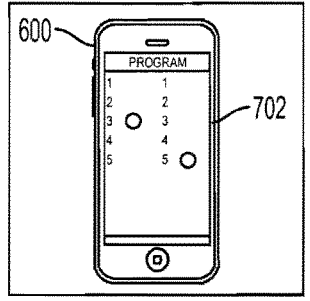
Figure 7F:
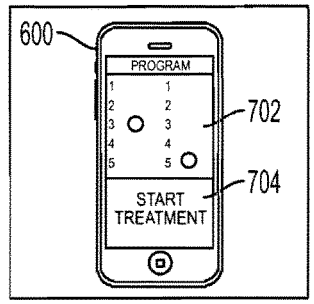
Figure 7G:
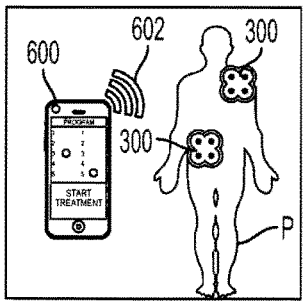
Figure 7H:
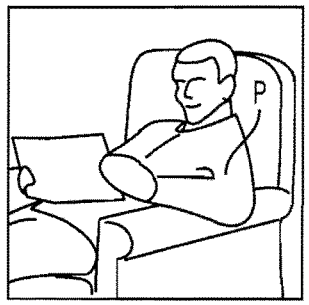
Figure 7I:
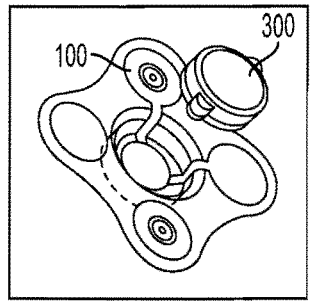
Figure 7J:
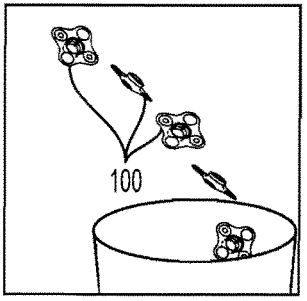
Figure 7K:
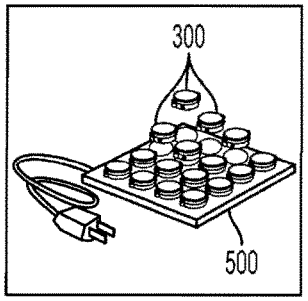
Figure 7L:
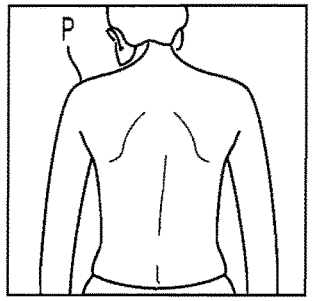

FIGS. 7A through 7L show steps in the use of the preferred embodiment. In FIG. 7A, the patient P is suffering from lower-back and shoulder pain. In FIG. 7B, the patient P peels off the cover 112 from the pad 100 and inserts a battery/controller pod 300. In FIG. 7C, the patient P places a pad, with the pod inserted, at each pain zone. In FIG. 7D, the patient P runs the smartphone application on the smartphone 600 and selects the transducer locations on the application's graphical user interface 702. The application can also prompt the patient on where to place the pads using diagrams or photographs taken by the doctor at the initial appointment. Of course, the order of performing the steps of FIGS. 7B-7C and the step of FIG. 7D could be reversed. In FIG. 7E, the patient P chooses a treatment program for each zone on the graphical user interface 702. The programs can be custom-designed by the user and saved and named if liked, or the doctor can set and lock each program. In FIG. 7F, the patient P presses the "Start Treatment" button 704 on the graphical user interface 702. The graphical user interface 702 can show intensity, program curves, and the like. The application can also play music or video or allow the patient to play a game. In FIG. 7G, the pods 300 and the smartphone 600 communicate wirelessly over the Bluetooth connection 602 to control each pod 300 to load and start the appropriate treatment to the zone where it is located. In FIG. 7H, the treatment programs are running, and the patient P can relax during treatment. In FIG. 7I, the treatment programs are finished, and the patient P removes each pad 100 and removes each pod 300 from its corresponding pad. In FIG. 7J, each pad, which is intended for a single use, is discarded. In FIG. 7K, the pods 300 are placed into an inductive charger 500. In FIG. 7L, the process ends, and the patient's pain is relieved.

The application can wirelessly transmit information after each treatment to the doctor for the patient's file. The details can include duration, program setting, date and time. The application can also provide regular reminders to help the patient tailor and follow treatment guidelines as fits the patient's schedule. Communication with the doctor's office can be by any suitable communication technology, e.g., the data connection or SMS functionality in the smartphone 600.

The use of a smartphone or tablet means less physical product to track, produce, repair, or update, since the application can be implemented on hardware that the patient likely already has. Alternatively, a dedicated device can be produced. Product updates can largely be done by releasing updates of the application. Such updates can upgrade the look/feel and performance of the user interface and the programs.

The product will conform to the patient's aesthetics because the patient has already chosen the device and the cover. The user interface can also include options to customize such things as the color schemes.

Figure 8:
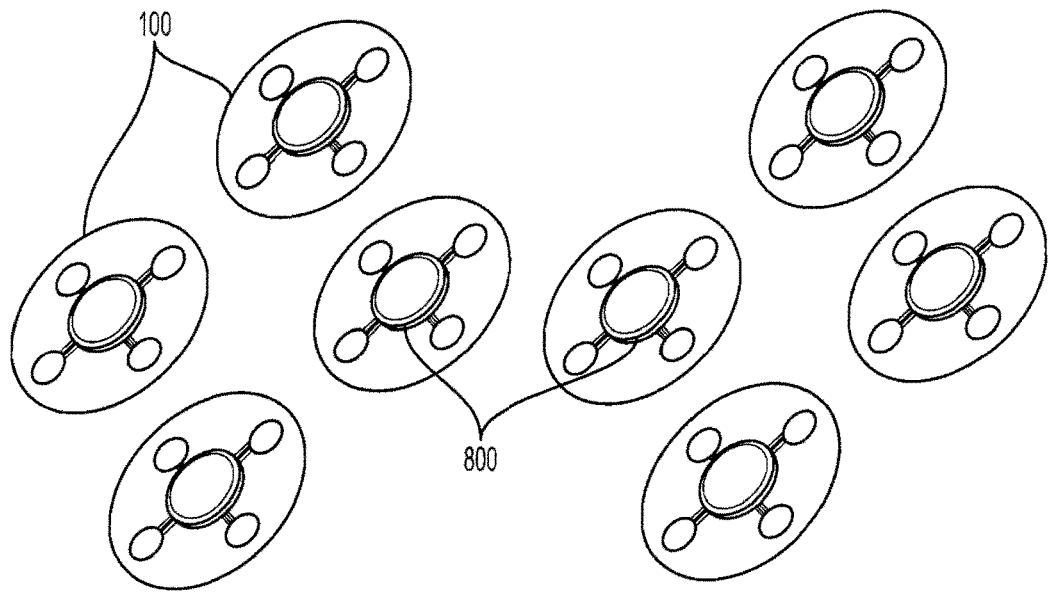
FIG. 8 is a drawing showing a possible modification of the pads.

Small, independent transducers (pad/pod combinations) make placement, coverage, and focus easier. In a variation of the preferred embodiment, shown in FIG. 8, changeable color-coded rings 800 provide a visual reference for placement and program options in the user interface.

Figure 9:
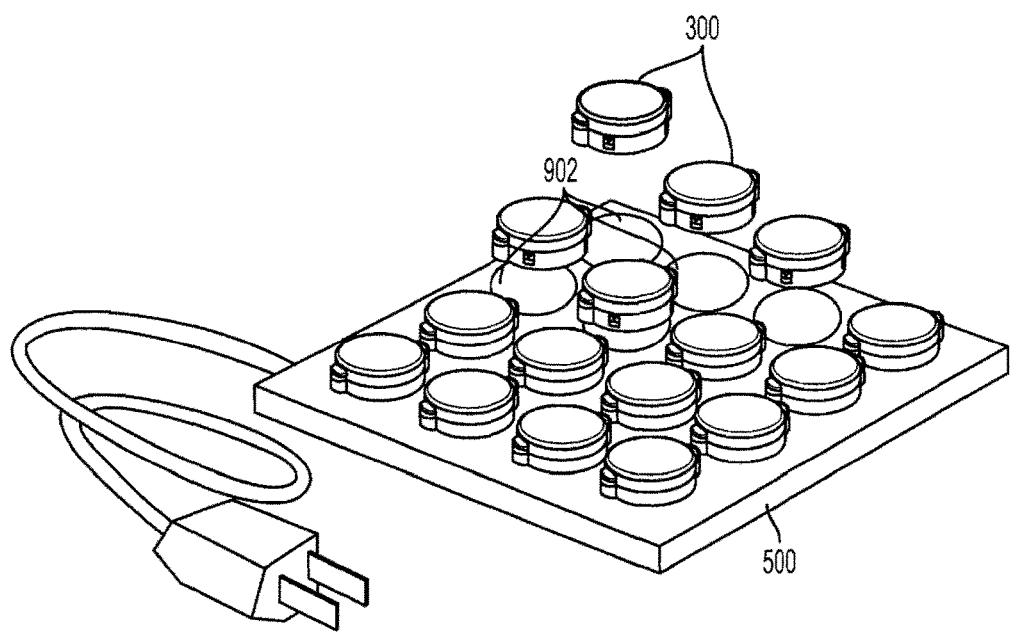
FIG. 9 is a drawing showing one possible configuration for the charger.

FIG. 9 shows an example of an inductive charging pad 500. The charging pad 500 has a dimple 902 into which each pod 300 can be snapped for charging. Some sort of contact charging can be provided instead.

Figure 10A:
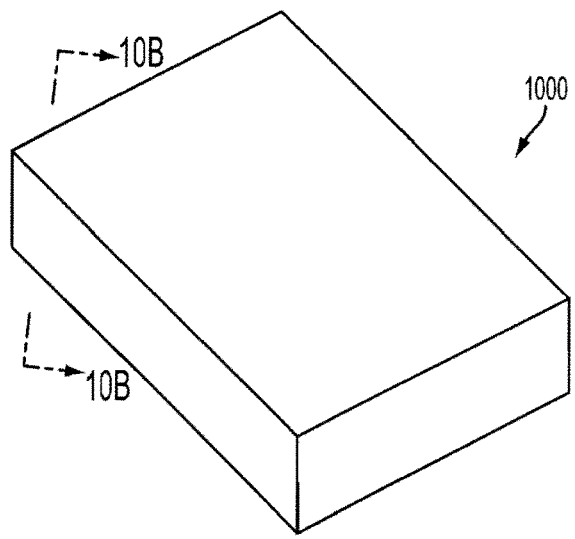
FIG. 10A is a perspective view showing another possible configuration for the charger.
Figure 10B:
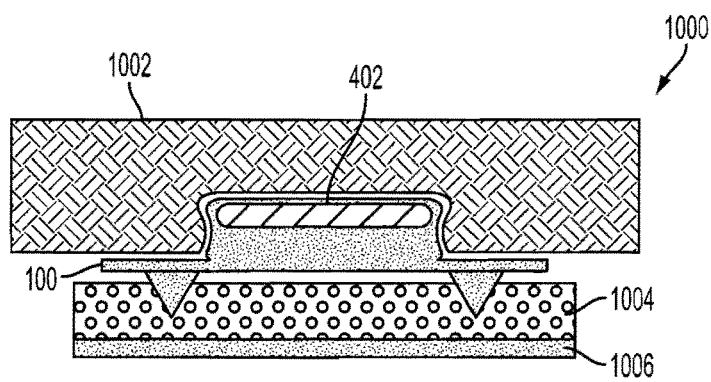
FIG. 10B is a cross-sectional view taken along lines XB-XB of FIG. 10A.

FIGS. 10A and 10B are a perspective view and a cross-sectional view, respectively, of a charging box 1000 that charges one side and disinfects the other side simultaneously. The box 1000 includes an inductive charging mat 1002 and a capillary foam 1004 for applying a sterilization fluid 1006 to the pod 300.

Figure 11:
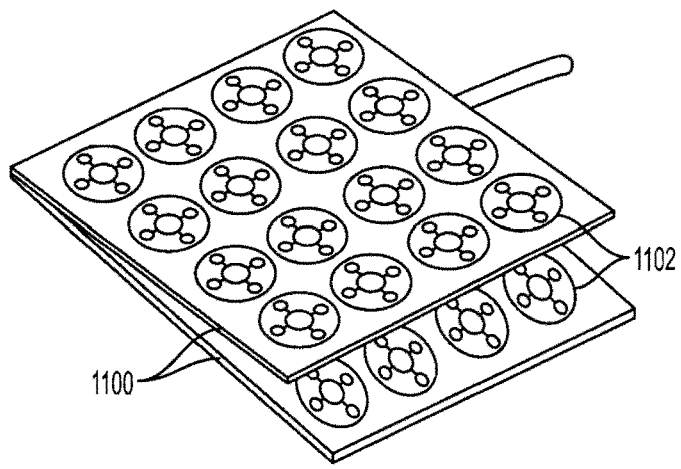
FIG. 11 is a drawing showing another possible modification of the pads.

FIG. 11 shows multiple sheets 1100 to keep different colored transducers 1102 separate. This can be useful if, for example, different types of transducers are provided.

While a preferred embodiment and variations thereon have been set forth in detail above, those skilled in the art who have reviewed the present disclosure will readily appreciate that other embodiments can be realized within the scope of the invention. For example, numerical values are illustrative rather than limiting, as are disclosures of specific technologies, technical standards, and methods of charging the pods. Therefore, the present invention should be construed as limited only by the appended claims.

What is claimed is:

1. A device for cutaneous field stimulation, the device comprising:
   a sealed and cleanable battery/controller pod including at least one battery; and
   a disposable pad that is configured such that the pod is insertable into a pocket of the pad, the pad comprising:
      a substrate;
      a plurality of TENS pads on the substrate, wherein the plurality of TENS pads generally surround the pocket;
      a plurality of CFS needle electrodes on the substrate; and
      circuitry on the substrate for conveying power from the pod to the plurality of TENS pads and the plurality of CFS needle electrodes, and the circuitry extends through the pocket to engage the pod.

2. The device of claim 1, wherein the pod comprises a microcontroller.

3. The device of claim 2, wherein the pod further comprises a communication device for wireless communication between the microcontroller and an external device.

4. The device of claim 1, further comprising a charger for the pod.

5. The device of claim 4, wherein the charger is an inductive charger.

6. The device of claim 4, wherein the charger comprises a component for disinfecting the pod while charging the pod.

7. A system for cutaneous field stimulation, the system comprising:
   a processing device;
   a plurality of sealed and cleanable battery/controller pods, each of the pods including at least one battery and each of the pods being configured for wireless communication with the processing device; and
   a plurality of disposable pads that are configured such that each pod is insertable into a pocket of one of the pads, each of the pads comprising TENS pads and CFS needle electrodes, wherein the TENS pads generally surround the pocket of the pad, wherein each pad has circuitry on a substrate for conveying power from the pod to the TENS pads and the CFS needle electrodes, and the circuitry of each pad extends through the pocket to engage the pod;
   wherein the processing device is configured to control the pods over the wireless communication to implement the cutaneous field stimulation.

8. The system of claim 7, wherein the processing device is a smartphone or tablet running an application for controlling the pods.

9. The system of claim 7, wherein the pads comprise at least two sets of pads, the at least two sets of pads being color-coded with different colors.

10. The system of claim 7, wherein each of the pods comprises:
    a microcontroller; and
    a communication device for wireless communication between the microcontroller and the processing device.

11. The system of claim 7, further comprising a charger for the pods.

12. The system of claim 11, wherein the charger is an inductive charger.

13. The system of claim 11, wherein the charger comprises a component for disinfecting the pod while charging the pod.

\* \* \* \* \*